United States Patent [19]
Sultenfuss

[11] Patent Number: 5,514,382
[45] Date of Patent: May 7, 1996

[54] DAILY VITAMIN AND MINERAL SUPPLEMENT FOR WOMEN

[76] Inventor: Sherry Sultenfuss, 102 Harbor View La., Largo, Fla. 34640

[21] Appl. No.: 324,780

[22] Filed: Oct. 17, 1994

[51] Int. Cl.⁶ ..................................................... A61K 9/68
[52] U.S. Cl. ...................... 424/440; 424/490; 424/195.1; 424/451
[58] Field of Search ..................... 424/440, 490, 424/195.1

[56] References Cited

U.S. PATENT DOCUMENTS 4,976,960  12/1990  Grossman et al. ............... 424/195.1
5,208,039   5/1993  Poupon et al. ...................... 424/490
5,270,063  12/1993  Wullschleger et al. .............. 426/73
5,326,569   7/1994  Acosta et al. ...................... 424/440

*Primary Examiner*—Thurman K. Page
*Assistant Examiner*—William E. Benston, Jr.

[57] ABSTRACT

A daily vitamin and mineral supplement for women comprising vitamin A, beta-carotene, niacin, riboflavin, pantothenic acid, pyridoxine, cyanocobalamin, biotin, para-aminobenzoic acid, inositol, choline, vitamin C, vitamin D, vitamin E, vitamin K, boron, calcium, chromium, copper, iodine, iron, magnesium, manganese, molybdenum, selenium, zinc and bioflavonoid. For women up to 40 years of age, iron is included. For women over 40 years of age, iron is optionally included.

10 Claims, 1 Drawing Sheet

U.S. Patent    May 7, 1996    5,514,382
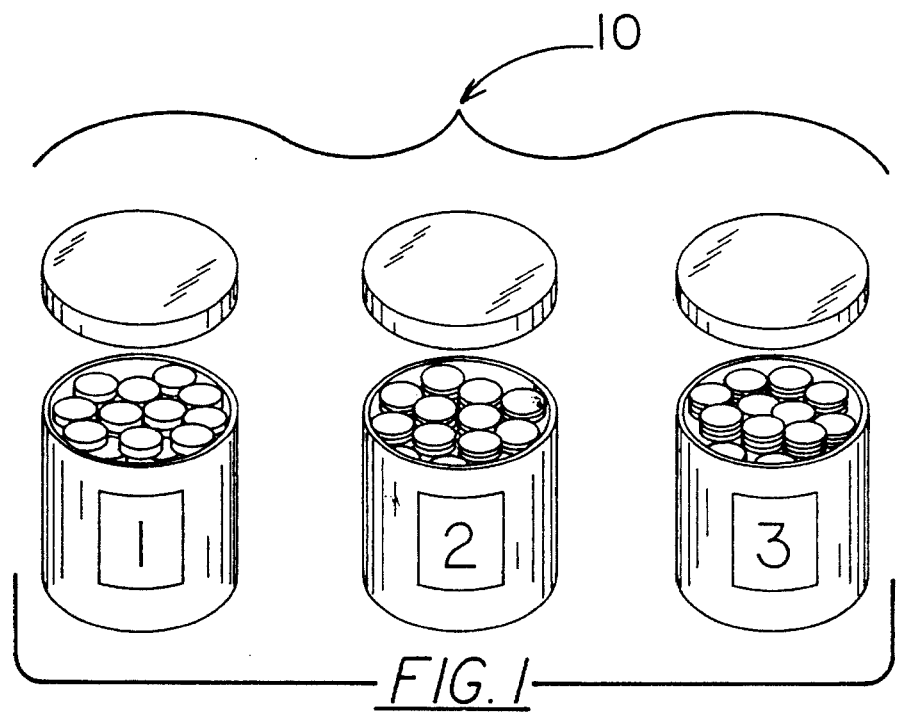
FIG. 1
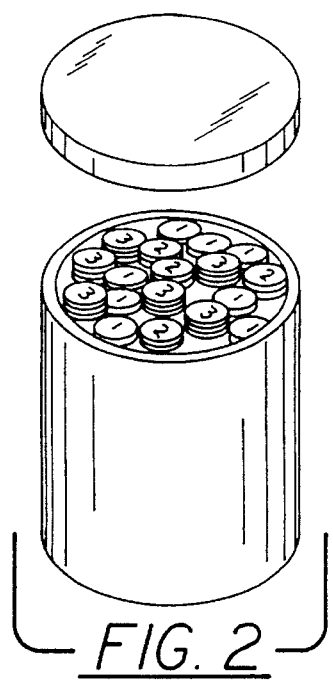
FIG. 2
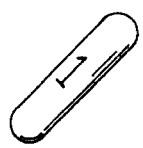         
FIG. 3        FIG. 4        FIG. 5        FIG. 6

DAILY VITAMIN AND MINERAL SUPPLEMENT FOR WOMEN

BACKGROUND OF THE INVENTION

1. Field of the Invention

The present invention relates to a daily vitamin and mineral supplement for women and more particularly pertains to providing the necessary nutrients for allowing women to maintain their present health and positively influence their future health with a daily vitamin and mineral supplement.

2. Description of the Prior Art

The use of vitamin and mineral supplements for women is known in the prior art. More specifically, vitamin and mineral supplements for women heretofore devised and utilized for the purpose of providing necessary daily nutrients are known to consist basically of familiar, expected and obvious structural configurations, notwithstanding the myriad of designs encompassed by the crowded prior art which have been developed for the fulfillment of countless objectives and requirements. While prior art supplements fulfill their respective, particular objective and requirements, the aforementioned patents do not describe a daily vitamin and mineral supplement for women that is specifically formulated to provide the necessary nutrients for allowing a women to maintain her present health and positively influence her future health.

In this respect, the daily vitamin and mineral supplement for women according to the present invention substantially departs from the conventional concepts and designs of the prior art, and in doing so provides an apparatus primarily developed for the purpose of providing the necessary nutrients for allowing women to maintain their present health and positively influence their future health.

Therefore, it can be appreciated that there exists a continuing need for a new and improved daily vitamin and mineral supplement for women which can be used for providing the necessary nutrients for allowing women to maintain their present health and positively influence their future health. In this regard, the present invention substantially fulfills this need.

SUMMARY OF THE INVENTION

In the view of the foregoing disadvantages inherent in the known types of vitamin and mineral supplements for women now present in the prior art, the present invention provides an improved daily vitamin and mineral supplement for women. As such, the general purpose of the present invention, which will be described subsequently in greater detail, is to provide a new and improved daily vitamin and mineral supplement for women and method which has all the advantages of the prior art and none of the disadvantages.

To attain this, the present invention essentially comprises, in combination, about 5,000 international units ±10% of vitamin A; between about 3 to 5 milligrams of beta-carotene; about 15 milligrams ±10% of thiamin; about 15 milligrams ±10% of riboflavin; about 30 milligrams ±10% of niacin; about 25 milligrams ±10% of pantothenic acid; about 50 milligrams ±10% of pyridoxine; about 400 micrograms ±10% of folic acid; about 50 micrograms ±10% of cyanocobalamin; about 50 micrograms ±10% of biotin; about 30 milligrams ±10% of para-aminobenzoic acid; about 80 milligrams ±10% of inositol; about 50 milligrams ±10% of choline; between about 500 to 1500 milligrams of vitamin C; about 400 international units ±10% of vitamin D; between about 400 to 800 milligrams of vitamin E; about 10 micrograms ±10% of vitamin K; about 3 milligrams ±10% of boron; between about 1,000 to 1,500 milligrams calcium; about 80 micrograms ±10% of chromium; about 2 milligrams ±10% of copper; about 150 milligrams ±10% of iodine; about 15 milligrams ±10% of iron; between about 400 to 600 milligrams of magnesium; about 5 milligrams ±10% manganese; about 15 micrograms ±10% molybdenum; about 50 micrograms ±10% selenium; about 20 milligrams ±10% zinc; and about 100 milligrams ±10% bioflavonoid.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved daily vitamin and mineral supplement for women which has all the advantages of the prior art vitamin and mineral supplements for women and none of the disadvantages.

It is another object of the present invention to provide a new and improved daily vitamin and mineral supplement for women which may be easily and efficiently manufactured and marketed.

It is a further object of the present invention to provide a new and improved daily vitamin and mineral supplement for women which is of durable and reliable construction.

An even further object of the present invention is to provide a new and improved daily vitamin and mineral supplement for women which is susceptible of a low cost of manufacture with regard to both materials and labor, and which accordingly is then susceptible of low prices of sale to the consuming public, thereby making such a daily vitamin and mineral supplement for women economically available to the buying public.

Still yet another object of the present invention is to provide a new and improved daily vitamin and mineral supplement for women which provides in the apparatuses and methods of the prior art some of the advantages thereof, while simultaneously overcoming some of the disadvantages normally associated therewith.

Even still another object of the present invention is to provide a new and improved daily vitamin and mineral supplement for women for providing the necessary nutrients for allowing women to maintain their present health and positively influence their future health.

Lastly, it is an object of the present invention to provide a new and improved daily vitamin and mineral supplement for women comprising vitamin A, beta-carotene, thiamin, niacin, riboflavin, pantothenic acid, pyridoxine, folic acid, cyanocobalamin, biotin, para-aminobenzoic acid, inositol, choline, vitamin C, vitamin D, vitamin E, vitamin K, boron, calcium, chromium, copper, iodine, iron, magnesium, manganese, molybdenum, selenium, zinc, and bioflavonoid.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of the preferred embodiment of the daily vitamin and mineral supplement for women constructed in accordance with the principles of the present invention, the three types of pills each being visually identifiable and with each type of pill being in its own specific identifiable container.

FIG. 2 is a perspective view of an alternate embodiment for storing the three types of pills, the pills being individually identifiable but stored in a common container.

FIGS. 3, 4, 5 and 6 are perspective illustrations of different types of pills with each pill being individually identifiable.

The same reference numerals refer to the same parts through the various Figures.

DESCRIPTION OF THE PREFERRED EMBODIMENT

With reference now to the drawings, and in particular to FIG. 1 thereof, the preferred embodiment of the new and improved daily vitamin and mineral supplement for women embodying the principles and concepts of the present invention and generally designated by the reference number 10 will be described.

The present invention is comprised of a plurality of components. In their broadest context, such components include several vitamins, various metals and non-metals, a halogen, and a complex carbon compound. Such components are individually configured and correlated with respect to each other to provide the intended function of providing a nutritional supplement for women up to 40 years of age and women over 40 years of age.

The present invention includes several vitamins. These vitamins include vitamin A, vitamin B, vitamin C, vitamin D, vitamin E, and vitamin K. Vitamin A provides many benefits. Vitamin A prevents night blindness and other eye disorders, keeps skin moist and elastic (including the eyes and vagina), maintains healthy hair and skin and gums, reduces risk of breast cancer, helps alleviate mastodynia, reduces the risk of lung cancer, maintains cell structure and integrity, works as an antioxidant to prevent cell aging and possibly atherosclerosis, helps prevent infection, and negates skin wrinkling and the effects of sun damage. Vitamin A is a fat soluble vitamin. The term vitamin A is used to include retinol and other chemically similar compounds referred to as "retanoids". These compounds are found in animal products. Vitamin A as beta-carotene is found mostly in fruits and vegetables and is not toxic at any known dose. Beta-carotene is a provitamin; it is only turned into retinol as the body requires. Beta-carotene is probably at least as important as retinol in maintaining health. For both women under 40 years of age and women over 40 years of age, the recommended daily dosage is 5,000 international units (IU) ±10% of vitamin A and between about 3 to 5 milligrams of beta-carotene. In the preferred embodiment, four milligrams of beta-carotene are used.

The B vitamins contained within the present invention are taken as a group in a B complex. There are eleven common B vitamins. They are all water-soluble and need to be replaced on a daily basis. The B vitamins consist of thiamin, riboflavin, niacin, pantothenic acid, pyridoxine, folic acid, cyanocobalamin, biotin, para-aminobenzoic acid, inositol, and choline. These eleven B vitamins form the B complex.

Thiamin is commonly referred to as vitamin B1. Thiamin helps keep collagen-rich connective and mucous membranes healthy. It also helps to maintain smooth muscle. Thiamin is also known to help in the formation of blood cells and it is necessary for proper nervous system function. In the preferred embodiment, the recommended daily dosage of thiamin for women under 40 years of age and women over 40 years of age is about 15 milligrams ±10%.

Riboflavin, commonly referred to as vitamin B2, is also provided. Riboflavin is necessary for healthy hair, nails, and mucous membranes. It is also important in red blood cell formation, antibody production, and overall growth. In the preferred embodiment, the recommended daily dosage of riboflavin for both women under 40 years of age and women over 40 years of age is about 15 milligrams ±10%.

The B vitamin niacin, commonly referred to as vitamin B3, is included. Niacin is a generic name for a common group of compounds that exhibit niacin activity. Nicotinic acid and niacinamide are most commonly used as vitamin supplements. Niacin helps in the production of most of the sex hormones. It dilates blood vessels, lowers cholesterol and helps maintain blood circulation. For women under 40 years of age, the recommended daily dosage of niacin is about 30 milligrams ±10%. For women over 40 years of age, the recommended daily dosage of niacin is about 100 milligrams ±10%.

The present invention also includes the B vitamin of pantothenic acid, commonly referred to as vitamin B5. Pantothenic acid is important for the production of adrenal gland hormones and supposedly increases overall energy levels. Pantothenic acid also helps convert food into energy. It is known as the "anti-stress" vitamin. In the preferred embodiment, for both women up to 40 years of age and women over 40 years of age, the recommended daily dosage of pantothenic acid is about 25 milligrams ±10%.

Another B vitamin provided is pyridoxine, commonly referred to as vitamin B6. Pyridoxine actually refers to and includes three different compounds in varying amounts: pyridoxine, pyridoxamine, and pyridoxal. In the present invention pyridoxine is used. Pyridoxine is probably involved in at least 100 different reactions in the body, from the production of ribonucleic acid (RNA) and deoxyribonucleic acid (DNA) to relieving water retention in women. In the preferred embodiment, for both women up to 40 years of age and women over 40 years of age, a daily dosage of about 50 milligrams +10% of pyridoxine is used.

Another B vitamin used is folic acid. Folic acid is essential in the production of red blood cells, the production of hormones, and the synthesis of DNA. In the preferred embodiment, for women up to 40 years of age and women over 40 years of age, about 400 micrograms ±10% of folic acid are used as a daily dosage.

Cyanocobalamin, commonly referred to as B12, is provided. Cyanocobalamin is necessary for overall metabolism and nervous system function. It is also essential for the metabolism of folic acid. Cyanocobalamin is needed to make red blood cells and is therefor necessary to prevent anemia. In the preferred embodiment, for women up to 40 years of age and women over 40 years of age, a daily dosage of about 50 micrograms ±10% of cyanocobalamin is included.

Biotin is another B vitamin that is part of the present invention. Biotin is necessary for the metabolism of carbohydrates, proteins, and fats. It is also needed for healthy hair and skin. In the preferred embodiment, for women up to 40 years of age and women over 40 years of age, about 50 micrograms ±10% of biotin are used.

Another B vitamin included in the present invention is para-aminobenzoic acid, commonly referred to as PABA. Para-aminobenzoic acid aids in the metabolism of proteins and the production of red blood cells. Para-aminobenzoic acid applied topically acts as a sunscreen. It blocks out dangerous ultraviolet B rays. In the preferred embodiment, for women up to 40 years of age and women over 40 years of age, about 30 milligrams ±10% of para-aminobenzoic acid are used as a daily dosage.

The B vitamin known as inositol in also provided. Inositol is essential for healthy hair. It helps remove fats from the arteries and the liver. It has been noted to be necessary for brain function. In the preferred embodiment, for women up to 40 years of age and women over 40 years of age, about 80 milligrams ±10% of inositol are used.

The last B vitamin included in the present invention is choline. Choline is necessary for nervous system and brain function. It is also important for gall bladder and liver function. In the preferred embodiment, for women up to 40 years of age and women over 40 years of age, about 50 milligrams ±10% of choline is used as a daily dosage.

Vitamin C is also included. Vitamin C is necessary for the synthesis of collagen. Vitamin C is also used as an antioxidant. Vitamin C fights infection, reduces inflammation, heals wounds, reduces risks of heart disease, lowers cholesterol, reduces risk of lung and stomach and esophageal cancers, reduces cervical epithelial abnormalities (as reflected by pap smears), inhibits N-nitrosamine (a carcinogen) and reduces the severity of colds. Vitamin C is also critical for maintaining healthy gums. For women up to 40 years of age and women over 40 years of age, the recommended daily dosage of vitamin C is between about 500 to 1500 of milligrams. In the preferred embodiment, a daily dosage of 1500 milligrams is used.

Vitamin D is also an essential vitamin that is included in the present invention. Vitamin D assists in the mineralization and calcification of bone, prevents rickets in children, prevents osteomalacia in adults, preserves bone and tooth growth, and lowers blood pressure. Vitamin D is a fat soluble vitamin. It is both a hormone and a vitamin. It can be produced in the skin with help from the sun's rays from a cholesterol compound and can also be absorbed from foods in the diet. In the preferred embodiment, for women up to 40 years of age and women over 40 years of age, a dosage of about 400 international units ±10% of vitamin D is used.

The fat soluble vitamin known as vitamin E is also provided. Vitamin E is used as an antioxidant. Vitamin E is needed for maintenance of cell membranes and for overall neurological health. Vitamin E relieves hot flashes, relieves mastodynia, helps in fighting fibrocystic breast disease, reduces mammary tumors, improves premenstrual syndrome (PAS) symptoms, reduces the risk of lung cancer, and reduces the risk of heart disease. Vitamin E is the generic name for a technical group of 8 compounds: 4 tocopherol-$\alpha$, $\beta$, $\gamma$, and $\sigma$. The $\alpha$ tocopherol is the most active form of vitamin E and is the compound utilized. In the preferred embodiment, for women up to 40 years of age and women over 40 years of age, a dosage between about 400 to about 800 milligrams of vitamin E is recommended. In the preferred embodiment, 800 milligrams are used.

The last vitamin included is Vitamin K. Vitamin K is an active blood clotting agent. Vitamin K also assists in the growth of bones. In the preferred embodiment, for both women up to 40 years of age and women over 40 years of age, 10 micrograms ±10% of vitamin K are used as a daily dosage.

The present invention also includes metals. The metals included are calcium, chromium, copper, iron, magnesium, manganese, molybdenum, potassium, and zinc. Calcium is used for building bones and teeth. Furthermore, it is needed for proper heart rhythms for conducting nerve impulses, and for relaxing and contracting muscle. Calcium also reduces risk of colon cancer and lowers blood pressure. For women up to 40 years of age, between about 1,000 to about 1,500 milligrams of calcium is used. For women over 40 years of age, between about 1,500 to 2,000 milligrams of calcium is used. In the preferred embodiment, for women up to 40 years of age, 1,200 milligrams are included. For women over 40 years of age, 1,500 milligrams are included.

Chromium is included in the present invention and assists in the regulation of glucose metabolism. Chromium is also used in the synthesis of fatty acids and cholesterol. Furthermore, chromium assists in transporting proteins, lowers low density lipoprotein (LDL) and raises high density lipoprotein (HDL) blood levels, and may protect against coronary artery disease. For women up to 40 years of age, about 80 micrograms ±10% of chromium are used. For women over 40 years of age, about 100 micrograms ±10% of chromium are used.

Copper is also provided. Copper helps keep blood vessels elastic. Copper is also needed for formation of elastin and collagen. Furthermore, copper functions as an iron oxidizer and is essential for proper functioning of the vitamin C included in the present invention in the amount previously set forth. In the preferred embodiment, for both women up to 40 years of age and women over 40 years of age, about 2 milligrams ±10% of copper are used.

Iron is also included in the present invention. Iron is used in the production of hemoglobin and myoglobin. For women up to 40 years of age, about 15 milligrams of iron ±10% are used. For women over 40 years of age, about 9 milligrams of iron ±10% are used. However, iron is a very controversial mineral for inclusion in a vitamin supplement. On one hand, it has been reported that many people suffer from anemia as a result of an iron deficiency. On the other hand, high levels of iron may be partly responsible for heart and liver disease. In particular, iron stores of women may increase to a unsatisfactory high level after menopause.

The present invention also includes magnesium. Magnesium is involved in many enzymatic reactions of the body. Magnesium is used in bone formation and growth. It prevents bone loss, and relaxes coronary arteries. Magnesium is also used in managing pre-eclampsia, treating cardiac arythemas, and managing diabetes. For women up to 40 years of age, the dosage of magnesium used is between about 400 to 600 milligrams. For women over 40 years of age, the dosage of magnesium used is between about 500 to 700 milligrams. For women up to 40 years of age, 500 milligrams of magnesium is the preferred dosage.

Manganese is also included. Manganese assists in bone growth, and helps in the prevention of osteoporosis. Manganese regulates production and release of insulin, metabolizes fats and proteins, and assists in transmission through the nerves. Manganese also assists in the production of milk and thyroxin. In the preferred embodiment, for women up to 40 years of age and women over 40 years of age, about 5 milligrams ±10% of manganese are used.

Molybdenum is also provided. Molybdenum metabolizes fats and plays a biochemical role in the functioning of enzymes. Molybdenum also plays a role in iron utilization. In the preferred embodiment, for women up to 40 years of age and women over 40 years of age, about 15 micrograms of molybdenum ±10% is utilized.

Lastly, the metal zinc is included as part of the present invention. Zinc is a required trace element for proper formation of DNA and RNA. Zinc is needed for the growth and sexual development of a woman. Zinc is required for proper alcohol metabolism. For women up to 40 years of age, about 20 milligrams of zinc ±10% is included. For women over 40 years of age, about 30 milligrams of zinc ±10% is included as a daily dosage.

The present invention also includes the non-metals of boron and selenium. Boron is used for maintaining healthy bones and allows increased absorption of calcium, magnesium, and phosphorus required to maintain health. In the preferred embodiment, for women up to 40 years of age and women over 40 years of age, about 3 milligrams ±10% of boron are used.

The non-metal selenium is an antioxidant. Selenium reduces risk of heart attack and heart disease and reduces risk of cancers. Selenium also protects against metal poisoning and is synergistic with vitamin E. In the preferred embodiment, for women up to 40 years of age and women over 40 years of age, about 50 micrograms ±10% of selenium are used.

The present invention also includes the halogen of iodine. Iodine helps to metabolize fats. Furthermore, it is necessary for proper thyroid function and reduces fibrocystic breast conditions. In the preferred embodiment, for both women up to 40 years of age and women over 40 years of age, about 150 milligrams ±10% of iodine is provided.

Lastly, the present invention also includes a complex carbon compound known as bioflavonoid. Bioflavonoid is a derivative of a flavon compound that helps maintain the capillary walls of the circulatory system, thereby reducing the likelihood of hemorrhaging. In the preferred embodiment, for women up to 40 years of age and women over 40 years of age, a daily dosage of 100 milligrams ±10% of bioflavonoid is used.

The present invention as described hereinabove is formed into a delivery mechanism for allowing its ready ingestion by a woman on a daily basis. The delivery mechanism is established when the present invention is formed into a plurality of pills or similar drug release forms (including capsules, tablets, and the like). For women up to 40, the preferred embodiment of the present invention is formed into three pills to be taken three times daily. This includes, for example, one in the morning, one in the afternoon, and one in the evening. For women over 40 years of age, the preferred embodiment of the present invention is formed into four pills with one of these pills containing only iron. This allows women over 40 years of age the flexibility of ingesting or not ingesting the iron, since it is not clear at this time whether ingestion of iron by women over 40 years of age has positive or deleterious effects. The fourth pill is the one containing only iron. Additionally, an alternate embodiment for women over 40 years of age is realized when the present invention is formed into three pills with only one of these pills including the iron. The embodiments of the present invention described hereinabove are specifically formulated to support a women's nutritional requirements throughout her life as opposed to prior art vitamin supplements.

As shown in FIG. 1, the three individual pills which make up the regimen of the present invention are each supported and retained in an individual container. Each container is marked with indicia, preferably in the form of numbers 1 and 2 and 3, to indicate the nature of the pill therein. All first pills are in the container marked 1. All second pills are in the container marked 2. All third pills are in the container marked 3. In addition, as an extra precaution, all the pills within any one container are individually identifiable from the pills of the other containers. The first pills of container 1 are of one common color and a common shape, that of a short cylinder. The second pills of container 2 are of the same shape of the other pills but are identifiable as the second pills since they are formed of two colors, in the shape of a short cylinder but one half of the pill being of one color and the other half of the pill being of the other color. The third pills, those of container 3, are also preferably of the same short cylinder shape as all other pills but are fabricated of three colors, the colors being different alonf the axial extents of the short cylinder of which the pills are configured.

In the FIG. 2 embodiment, all of the pills, including the first pills, second pills and third pills, are all in a common container. The pills, however, are individually identifiable in that pills 1 are of a common color, pills 2 are of two distinct colors, and pills 3 are of three different colors. In addition, the pills are further identifiable in that the first pills of one color are also marked with the numeral 1, and the second pills of two colors are also marked with the numeral 2 and the third pills of three colors are marked with the numeral 3.

A further alternate embodiment of the invention is shown in FIGS. 3, 4, 5 and 6. In such embodiment, the four types of pills are marked with indicia in the form of numerals 1, 2, 3 and 4 for identification purposes. In addition, each pill is of a distinctive shape. Pill 1 is formed as an elongated capsule with parallel sides and rounded ends. Pill 2 is formed in a spherical shape. Pill 3 is formed in the shape of a short cylinder. Pill 4 is in the shape of an oval, generally egg-shaped in configuration. In addition to their distinctive shapes as a form of indicia, the pills are also marked with the numerals 1, 2, 3 and 4 as a supplemental distinguishing characteristic of indicia.

In using the pills for women under 40, pills 1, 2 and 3 are formulated so that only one of the pills has the desired iron supplement. Such pills would not be used by women over 40. In an alternate embodiment, for women over 40, pills 1, 2 and 3 would have all the desired vitamins except for iron. Such pills could be taken by all women regardless of age. In such situations, a fourth pill, a pill with iron, would be added for women under 40. Such fourth pill would include the iron to be excluded by women over 40 but included for women under 40.

As used herein, the term pill is intended to embrace any and all of the delivery techniques and mechanisms used for providing vitamins or the like, whether in the form of liquid, solid, particulate, etc., to a user and includes capsules, tablets and the like.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A daily vitamin and mineral supplement only for women up to 40 years of age comprising:
   about 5,000 international units ±10% of vitamin A;
   between about 3 to 5 milligrams of beta-carotene;
   about 15 milligrams ±10% of thiamin;
   about 15 milligrams ±10% of riboflavin;
   about 30 milligrams ±10% of niacin;
   about 25 milligrams ±10% of pantothenic acid;
   about 50 milligrams ±10% of pyridoxine;
   about 400 micrograms ±10% of folic acid;
   about 50 micrograms ±10% of cyanocobalamin;
   about 50 micrograms ±10% of biotin;
   about 30 milligrams ±10% of para-aminobenzoic acid;
   about 80 milligrams ±10% of inositol;
   about 50 milligrams ±10% of choline;
   between about 500 to 1500 milligrams of vitamin C;
   about 400 international units ±10% of vitamin D;
   between about 400 to 800 milligrams of vitamin E;
   about 10 micrograms ±10% of vitamin K;
   about 3 milligrams ±10% of boron;
   between about 1,000 to 1,500 milligrams calcium;
   about 80 micrograms ±10% of chromium;
   about 2 milligrams ±10% of copper;
   about 150 milligrams ±10% of iodine;
   about 15 milligrams ±10% of iron;
   between about 400 to 600 milligrams of magnesium;
   about 5 milligrams ±10% manganese;
   about 15 micrograms ±10% molybdenum;
   about 50 micrograms ±10% selenium;
   about 20 milligrams ±10% zinc; and
   about 100 milligrams ±10% bioflavonoid.

2. A daily vitamin and mineral supplement only for women over 40 years of age comprising:
   about 5,000 international units ±10% of vitamin A;
   between about 3 to 5 milligrams of beta-carotene;
   about 15 milligrams ±10% of thiamin;
   about 100 milligrams ±10% of niacin;
   about 15 milligrams ±10% of riboflavin;
   about 25 milligrams ±10% of pantothenic acid;
   about 50 milligrams ±10% of pyridoxine;
   about 400 micrograms ±10% of folic acid;
   about 50 micrograms ±10% of cyanocobalamin;
   about 50 micrograms ±10% of biotin;
   about 30 milligrams ±10% of para-aminobenzoic acid;
   about 80 milligrams ±10% of inositol;
   about 50 milligrams ±10% of choline;
   between about 500 to 1500 milligrams of vitamin C;
   about 400 international units ±10% of vitamin D;
   between about 400 to 800 milligrams of vitamin E;
   about 10 micrograms ±10% of vitamin K;
   about 3 milligrams ±10% of boron;
   between about 1,500 to 2,000 milligrams calcium;
   about 100 micrograms ±10% of chromium;
   about 2 milligrams ±10% of copper;
   about 150 milligrams ±10% of iodine;
   about 9 milligrams ±10% of iron;
   between about 500 to 700 milligrams of magnesium;
   about 5 milligrams ±10% of manganese;
   about 15 micrograms ±10% of molybdenum;
   about 50 micrograms ±10% of selenium;
   about 30 milligrams ±10% of zinc; and
   about 100 milligrams ±10% of bioflavonoid.

3. The daily vitamin and mineral supplement as set forth in claim 1 wherein the vitamin and mineral supplement is formed into a plurality of oral dosage forms for ingestion on a daily basis.

4. The daily vitamin and mineral supplement as set forth in claim 1 wherein the vitamin and mineral supplement is formed into three oral dosage forms for ingestion on a daily basis.

5. The daily vitamin and mineral supplement as set forth in claim 2 wherein the daily vitamin and mineral supplement is formed into four oral dosage forms for ingestion on a daily basis and with one of these pills containing only the iron.

6. The daily vitamin and mineral supplement as set forth in claim 2 wherein the daily vitamin and mineral supplement is formed into three oral dosage forms for ingestion on a daily basis and wherein the iron is contained in only one of these pills.

7. A daily vitamin and mineral supplement only for women comprising:
   a plurality of oral dosage forms, each of the oral dosage forms having a different portion of the vitamins and minerals needed for daily supplements for women, each of the oral dosage forms being individually identifiable one from another.

8. The supplement as set forth in claim 7 wherein three oral dosage forms are utilized with each oral dosage form containing about one-third of the needed supplements.

9. The supplement as set forth in claim 8 wherein iron is included in a fourth pill.

10. The supplement as set forth in claim 8 wherein iron is included in one of the pills only.

* * * * *